United States Patent [19]

Salzburg et al.

[11] Patent Number: 4,556,649

[45] Date of Patent: Dec. 3, 1985

[54] SUBSTITUTED MALONIC ACID DIAMIDE INSECTICIDES, COMPOSITIONS AND USE

[75] Inventors: Herbert Salzburg; Rudolf Fauss, both of Cologne; Kurt Findeisen, Odenthal; Bernhard Homeyer, Leverkusen, all of Fed. Rep. of Germany

[73] Assignee: Bayer Aktiengesellschaft, Leverkusen, Fed. Rep. of Germany

[21] Appl. No.: 684,570

[22] Filed: Dec. 21, 1984

[30] Foreign Application Priority Data

Jan. 7, 1984 [DE] Fed. Rep. of Germany ....... 3400401

[51] Int. Cl.$^4$ .................... A01N 37/20; A01N 43/84; C07C 103/24; C07D 295/14

[52] U.S. Cl. .................................. 514/63; 544/122; 544/132; 514/228; 544/131; 514/229; 544/133; 544/137; 514/230; 544/138; 544/139; 514/232; 544/146; 544/152; 514/234; 544/165; 544/168; 514/241; 544/215; 544/229; 514/256; 544/335; 514/316; 546/14; 546/187; 514/331; 546/191; 546/193; 514/357; 546/209; 546/210; 514/364; 546/212; 546/214; 514/365; 546/233; 546/336; 514/378; 548/110; 548/125; 514/383; 548/143; 548/205; 514/400; 548/255; 548/262; 514/452; 549/4; 549/76; 514/466; 549/214; 549/366; 514/471; 549/419; 514/488; 549/441; 549/496; 514/489; 536/419; 560/106; 514/517; 560/32; 560/163; 514/518; 560/251; 514/522; 564/86; 564/154; 514/534; 564/156; 260/456 R; 514/546; 260/456 NS; 260/456 P; 514/601; 260/463; 514/604; 260/465 D; 514/605; 514/616; 544/69; 544/86; 544/112

[58] Field of Search ............... 544/86, 131, 165, 69, 544/137, 168, 112, 138, 215, 122, 139, 335, 132, 146, 335, 133, 152, 229; 546/187, 191, 193, 209, 210, 212, 214, 233, 336, 14; 548/205, 125, 143, 255, 262, 342, 110; 549/76, 366, 214, 441, 496, 4; 556/419; 560/106, 251, 32, 163; 564/86, 156, 154; 260/456 R, 456 NS, 456 P, 465 D, 463; 514/63, 228, 229, 230, 232, 234, 241, 256, 316, 331, 357, 364, 365, 378, 383, 400, 452, 466, 471, 488, 489, 517, 518, 522, 534, 546, 601, 604, 605, 616

[56] References Cited

FOREIGN PATENT DOCUMENTS 2531836 2/1976 Fed. Rep. of Germany .

Primary Examiner—Robert W. Ramsuer

Attorney, Agent, or Firm—Sprung Horn Kramer & Woods

[57] ABSTRACT

Insecticidally active novel substituted malonic acid diamide insecticides of the formula

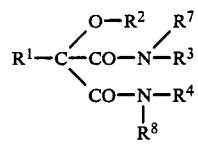

wherein
$R^1$ represents aryl or heteroaryl, each of which can optionally be substituted,
$R^2$ represents hydrogen or trialkylsilyl, and represents alkyl, cycloalkyl, alkenyl, alkinyl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl or arylalkylaminosulphonyl, each of which can optionally be substituted, and represents radicals of the formula

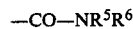

wherein
$R^5$ and $R^6$ independently of one another represent hydrogen, alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, it being possible for these radicals to be optionally substituted,
$R^3$ represents hydrogen or the radical $R^4$,
$R^7$ and $R^8$ independently of one another represent hydrogen, alkyl or aryl, and
$R^4$ represents a radical of the formula

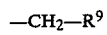

and
$R^9$ represents hydroxyl, alkoxy or aryloxy, each of which is optionally substituted, and alkylamino, arylamino, aralkylamino, dialkylamino, diarylamino, cycloalkylamino, alkenylamino, or nitrogen-containing saturated heterocyclic radicals which are bonded via N and which optionally contain further hetero atoms.

8 Claims, No Drawings

SUBSTITUTED MALONIC ACID DIAMIDE INSECTICIDES, COMPOSITIONS AND USE

The present invention relates to new substituted malonic acid derivatives, processes for their preparation, and their use as pest-combating agents.

It has been disclosed that malonic acid derivatives, such as 3,4-dichlorophenyl-malonic acid diamide, possess insecticidal activity (application Ser. No. 419,100, filed Sept. 16, 1982, corresponding to German Published Specification DE-OS 3,140,275). Their action is not always satisfactory when low concentrations are used.

It has been found that the substituted malonic acid derivatives of the general formula I are outstandingly suitable for combating pests:

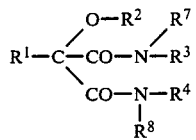

in which
R$^1$ represents aryl or heteroaryl, each of which can optionally be substituted,
R$^2$ represents hydrogen or trialkylsilyl, and represents alkyl, cycloalkyl, alkenyl, alkinyl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl or arylalkylaminosulphonyl, each of which can optionally be substituted, and represents radicals of the formula

—CO—NR$^5$R$^6$ wherein
R$^5$ and R$^6$ independently of one another represent hydrogen, alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, it being possible for these radicals to be optionally substituted,
R$^3$ represents hydrogen or the radical R$^4$, R$^7$ and R$^8$ independently of one another represent hydrogen, alkyl or aryl, and
R$^4$ represents the radical of the formula

—CH$_2$—R$^9$ wherein
R$^9$ represents hydroxyl, alkoxy or ayloxy, each of which can optionally be substituted, alkylamino, cycloalkylamino, arylamino, dialkylamino, alkenylamino, diarylamino, aralkylamino or nitrogen-containing saturated heterocyclic radicals which are bonded via N and which optionally contain further hetero atoms.

It has furthermore been found that the compounds of the formula I

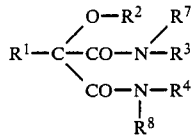

wherein
R$^1$ represents aryl or heteroaryl, each of which can optionally be substituted,
R$^2$ represents hydrogen or trialkylsilyl, and represents alkyl, cyloalkyl, alkenyl, alkinyl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl or arylalkylaminosulphonyl, each of which can optionally be substituted, and represents radicals of the formula

—CO—NR$^5$R$^6$ wherein
R$^5$ and R$^6$ independently of one another represent hydrogen, alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, it being possible for these radicals to be optionally substituted,
R$^3$ represents hydrogen or the radical R$^4$,
R$^7$ and R$^8$ represent hydrogen, alkyl or aryl, and
R$^4$ represents a radical of the formula

—CH$_2$—R$^9$ wherein
R$^9$ represents hydroxyl, alkoxy or aryloxy, each of which can optionally be substituted, alkylamino, arylamino, aralkylamino, dialkylamino, diarylamino, cycloalkylamino, alkenylamino, or nitrogen-containing saturated heterocyclic radicals which are bonded via N and optionally contain further nitro atoms,
are obtained by a process in which compounds of the formula II

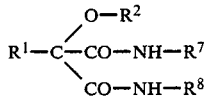

wherein
R$^1$, R$^2$, R$^7$ and R$^8$ have the meaning given above, are reacted with formaldehyde or formaldehyde-donating compounds in the presence of an acid or base and, if appropriate, simultaneously or subsequently with alkylamines, cycloalkylamines, alkenylamines, arylamines, dialkylamines, diarylamines, aralkylamines or N-containing saturated heterocyclic compounds which optionally can contain further hetero atoms, or with aliphatic or aromatic OH compounds.

The substituted malonic acid derivatives according to the invention are particularly suitable for combating insects and spider mites. Moreover, they are distinguished by a substantially better action than the compounds known for these indications from the prior art.

They also possess advantageous properties in respect of toxicity to warm-blooded animals.

Preferred new substituted malonic acid derivatives of the general formula I are those in which $R^1$ represents phenyl which can optionally be substituted by one or more identical or different radicals from amongst the following radicals: halogen, in particular chlorine, bromine or fluorine, nitro, amino, OH, CN, $C_{1-4}$-alkyl, in particular methyl, $C_{1-4}$-halogenoalkyl, in particular trifluoromethyl, trichloromethyl or pentafluoroethyl, $C_{1-4}$-alkoxy, methylenedioxy, ethylenedioxy, $C_{1-4}$-halogenoalkoxy, in particular trifluoromethoxy, pentafluoroethoxy, difluoromethylenedioxy, halogen-substituted ethylenedioxy, $C_{1-4}$-alkylthio, $C_{1-4}$-halogenoalkylthio, in particular trifluoromethylthio, $C_{2-8}$-alkoxyalkyl, $C_{2-8}$-halogenoalkoxyalkyl, $C_{1-4}$-alkylsulphonyl, in particular methylsulphonyl, $C_{1-4}$-halogenoalkylsulphonyl, carboxyl, carbalkoxy, in particular methoxycarbonyl, and the radical $C_{1-4}$-alkoxy-N=CH—, in particular $CH_3O$—N=CH—, or phenyl, phenoxy, thiophenyl which can optionally be substituted by halogen or $C_{1-4}$-alkyl, and carboxyalkoxy having 2–4 C atoms, such as carboxymethoxy.

$R^1$ furthermore preferably represents heteroaryl, such as pyridinyl, pyrimidinyl, triazinyl, isoxazolyl, thiazolyl, oxadiazolyl, imidazolyl, triazolyl, furanyl or thiophenyl, each of which can optionally be monosubstituted or polysubstituted by identical or different substituents from amongst halogen, in particular chlorine, $C_{1-4}$-alkyl, in particular methyl or ethyl, and $C_{1-4}$-alkoxy, in particular methoxy or ethoxy.

$R^1$ furthermore preferably represents 3-nitrophenyl, 3-iodophenyl, biphenyl, 4-trimethylsilyoxyphenyl, 4-chloro3-nitrophenyl, 3-chloro-4-nitrophenyl, 3,4,5-trichlorophenyl, 3,5-dichloro-4-fluorophenyl, 4-difluoromethylphenyl, 3-nitro-4-fluorophenyl, 3-fluoro-4-nitrophenyl, 3-trifluoromethyl-4-chlorophenyl, 4-trifluoromethyl-3-chlorophenyl, 3-chloro-5-trifluoromethylphenyl, 3,4-(di(trifluoromethyl)-phenyl, 3-trifluoromethyl-4,5-dichlorophenyl, 4-trifluoromethyl-3,5-dichlorophenyl, 4-trifluoromethoxy-3-nitrophenyl, 4-trifluoromethoxy-3-bromophenyl, 4-nitro-3-trifluoromethoxyphenyl, 4-bromo-3-trifluoromethoxphenyl, 3-nitro-4-trifluoromethoxy-5-chlorophenyl, 4-methoxy-3,5-dichlorophenyl, 4-methyl-3,5-dichlorophenyl, 4-fluoro-3-bromophenyl, 4-bromo-3-fluorophenyl, 4-chloro-3-methylphenyl, 4-trifluoromethylmercaptophenyl, 4-trifluoromethoxy-3-chlorophenyl, 3-trifluoromethyl-4-chlorophenyl, 4-chlorodifluoromethoxy-3-chlorophenyl, 4-fluoro-3-chlorophenyl, pentafluorophenyl, 4-fluoro-3,5-dibromophenyl, 4-fluoro-3-chloro-5-bromophenyl, 4-chloro-3,5-dibromophenyl, 4-bromo-3,5-dichlorophenyl, 3-bromo-4,5-dichlorophenyl, 3,4,5-trifluorophenyl, 3,4,5-tribromophenyl, 4-amino-3,5-dichlorophenyl or 4-hydroxy-3,5-dichlorophenyl.

Preferred compounds of the formula I are those in which $R^2$ represents hydrogen, trialkylsilyl having 1–4 C atoms in the alkyl part, $C_{1-4}$-alkyl, $C_{1-4}$-alkylcarbonyl, benzoyl which can optionally be substituted by one or more identical or different radicals from amongst the following radicals (A). (A) represents halogen, in particular chlorine, bromine or fluorine, nitro, amino, CN, $C_{1-4}$-alkyl, in particular methyl, $C_{1-4}$-halogenoalkyl, in particular trifluoromethyl or pentafluoroethyl, $C_{1-4}$alkoxy, $C_{1-4}$-halogenoalkoxy, in particular trifluoromethoxy, pentafluoroethoxy, methylenedioxy, ethylenedioxy or difluoromethylenedioxy, halogen-substituted ethylenedioxy, such as trifluoroethylenedioxy, $C_{1-4}$-alkylthio, $C_{1-4}$-halogenoalkylthio, in particular trifluoromethylthio, $C_{2-8}$-alkoxyalkyl, $C_{2-8}$-halogenoalkoxyalkyl, $C_{1-5}$-alkylsulphenyl or phenylsulphenyl, each of which can optionally be substituted, $C_{1-4}$-alkylsulphonyl, in particular methylsulphonyl, $C_{1-4}$-halogenoalkylsulphonyl, carbalkoxy, in particular methoxycarbonyl, and the radical $C_{1-4}$-alkoxy-N=CH—, in particular $CH_3$-O-N=CH—, or represents phenyl, phenoxy or thiophenyl, each of which can optionally be substituted by halogen or $C_{1-4}$-alkyl, and represents carboxyalkoxy having 2–4 C atoms, such as carboxymethoxy;

$R^2$ furthermore preferably represents $C_{1-4}$-alkoxycarbonyl, phenoxycarbonyl which can optionally be substituted by one or more radicals (A), or preferably represents C1-4-alkylsulphonyl, phenylsulphonyl which can optionally be substituted by one or more radicals (A), or preferably represents $C_{1-4}$-alkylaminosulphonyl, $C_{1-5}$-alkylsulphenyl or phenylsulphenyl, each of which can optionally be substituted, di-$C_{1-4}$-alkylaminosulphonyl, phenylaminosulphonyl which can optionally be substituted by one or more radicals (A), or represents phenyl-$C_{1-4}$-alkylaminosulphonyl.

Preferred compounds of the formula I are those in which $R^3$ represents hydrogen or the radical $R^4$.

$R^7$ and $R^8$ preferably represent hydrogen or $C_{1-4}$-alkyl, or preferably represent phenyl which is optionally substituted by halogen. Hydrogen and methyl are very particularly preferred.

$R^4$ preferably represents $$-CH_2-R^9$$

wherein $R^9$ represents hydroxyl, $C_{1-4}$-alkoxy, phenoxy which can optionally be substituted by one or more radicals (A), or represents $C_{1-8}$-alkylamino, $C_{5-6}$-cycloalkylamino, phenylamino which is optionally substituted by one or more radicals (A), or represents di-$C_{1-8}$-alkylamino, phenyl-$C_{1-4}$-alkylamino, or saturated nitrogen-containing heterocyclic compounds which are bonded via N and have 5–6 ring atoms, such as morpholine, pyrimidine or piperidine.

Particularly preferred compounds of the formula I are those in which $R^1$ represents phenyl which is optionally substituted by halogen, in particular fluorine or chlorine, $C_{1-4}$-alkyl, in particular methyl, $C_{1-4}$-alkoxy, $C_{1-4}$-halogenoalkoxy, $C_{1-4}$-halogenoalkyl, $NH_2$, $CH_3O$-N=CH—or nitro.

Compounds of the general formula I which may be very particularly mentioned are those in which $R^1$ represents phenyl which is optionally monosubstituted to trisubstituted in the 3-, 4-, or 5-position by identical or different substituents from amongst halogen, in particular fluorine, chlorine, bromine or iodine, $R^2$ represents $C_{1-4}$-alkyl, in particular methyl, optionally halogen-substituted $C_{1-4}$-alkylaminosulphonyl, $C_{1-4}$-alkylcarbonyl, in particular methylcarbonyl, optionally halogen-substituted phenylcarbonyl, phenylsulphenyl, $C_{1-4}$-alkylsulphenyl or trialkylsilyl, in particular trimethylsilyl, and represents —CO—NR$^5$R$^6$, wherein
R$^5$ represents hydrogen and R6 represents optionally halogen-substituted phenyl or phenylcarbonyl, or represents $C_{1-4}$-alkyl or $C_{1-4}$-alkylcarbonyl,
R$^4$ represents —CH$_2$—R$^9$, wherein
R$^9$ represents $C_{1-4}$-alkylamino, phenylamino, $C_{2-8}$dialkylamino, morpholino or piperidino.

Compounds of the formula I which may be particularly mentioned are those in which
R$^1$ represents phenyl which is optionally monosubstituted or polysubstituted by chlorine, and
R$^2$ represents hydrogen or trimethylsilyl,
R$^3$ represents hydrogen or R$^4$, and
R$^4$ represents methylamino, ethylamino, morpholino or piperidino.

$$R^1-\underset{\underset{CON\diagdown R^8}{|}}{\overset{\overset{OR^2}{|}}{C}}-CON\diagdown \overset{R^3}{\underset{R^4\diagdown R^7}{}} \qquad I$$

| R$^1$ | R$^2$ | R$^3$ | R$^4$ | R$^7$ | R$^8$ |
|---|---|---|---|---|---|
| 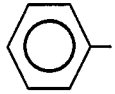 | —H | —H | —CH$_2$OCH$_3$ | —H | —H |
| 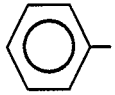 | —H | —CH$_2$OCH$_3$ | —CH$_2$OCH$_3$ | —H | —H |
| 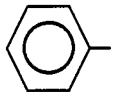 | —CH$_3$ | —H | —CH$_2$OH | —H | —H |
| 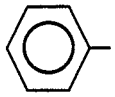 | —H | —CH$_3$ | —CH$_2$NH—C$_6$H$_5$ | —CH$_3$ | —CH$_2$NH—C$_6$H$_5$ |
| 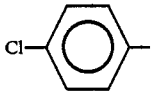 | —H | —H | —CH$_2$OC$_2$H$_5$ | —H | —H |
| 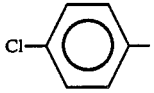 | —H | —CH$_2$OCH$_3$ | —CH$_2$OCH$_3$ | —H | —H |
| 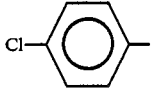 | —CH$_3$ | —CH$_2$OH | —CH$_2$OH | —CH$_3$ | —CH$_3$ |
| 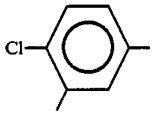 | —H | —CH$_2$OC$_2$H$_5$ | —CH$_2$OC$_2$H$_5$ | —H | —H |
| 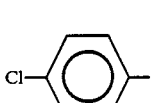 | —H | —CH$_2$N(CH$_3$)$_2$ | —CH$_2$N(CH$_3$)$_2$ | —CH$_3$ | —CH$_3$ |

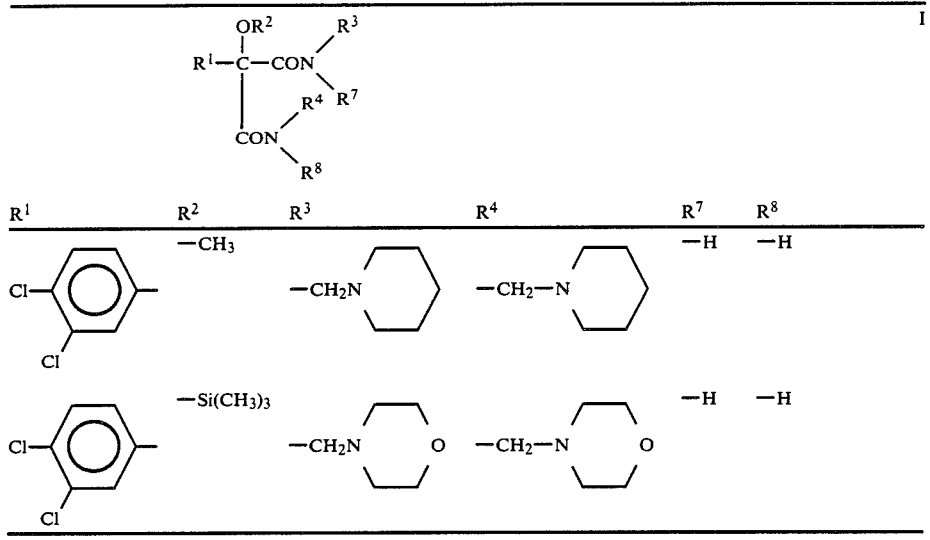

The reaction of the compounds of the formula II with formaldehyde is carried out, if appropriate, in the presence of acid acceptors and, if appropriate, in the presence of a diluent. The course of the reaction can be represented by, for example, the following equation:

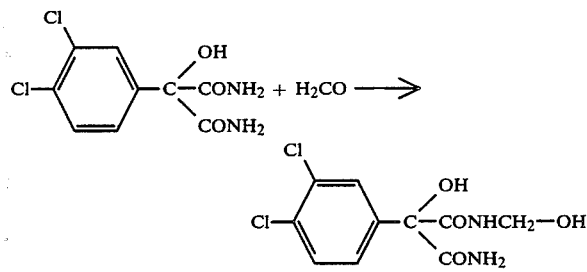

Formaldehyde is employed in amounts from an equimolar amount to about a 10-fold excess.

Preferably used compounds of the formula II are those in which the substituents $R^3$ and $R^4$ have the meanings mentioned as being preferred in the case of the compounds of the formula I. Compounds of the formula II are known (application Ser. No. 419,100, filed Sept. 16,1982, corresponding to German Published Specification DE-OS 3,140,27. They can be prepared by the process there. The following compounds of the formula II may be mentioned individually: Phenylhydroxy-malonic acid diamide, 2-, 3- and 4-chlorophenylhydroxy-malonic acid diamide, 2,3-dichlorophenylhydroxy-malonic acid diamide, 3,4-dichlorophenyl-hydroxymalonic acid diamide, 3,5-dichlorophenyl-hydroxy-malonic acid diamide, 2,4-dichlorophenyl-hydroxy-malonic acid diamide, 2,5-dichlorophenyl-hydroxy-malonic acid diamide, 2,6-dichlorophenyl-hydroxy-malonic acid diamide, 2-, 3- and 4-nitrophenyl-hydroxy-malonic acid diamide, 2-chloromethylphenyl-hydroxy-malonic acid diamide, 2-, 3- and 4-trifluoromethylphenyl-hydroxy-malonic acid diamide, 2-, 3- and 4-methoxyphenyl-hydroxy-malonic acid diamide, 2,6-dimethoxyphenyl-hydroxy-malonic acid diamide, 2-, 3- and 4-tolyl-hydroxy-malonic acid diamide, 2-, 3- and 4-trifluoromethoxyphenyl-hydrozy-malonic acid diamide, 2-, 3- and 4-fluorophenyl-hydroxymalonic acid diamide, 3,4-dichlorophenyl-hydroxy-malonic acid amide methylamide, phenyl-hydroxy-malonic acid diethylamide amide, 3,5-dichlorophenyl-hydroxy-malonic acid amide morpholinylamide, 3,4-dichlorophenyl-hydroxy-malonic acid-bis-isopentylamide, phenylhydroxy-malonic acid-bismethylamide, cyclohexyl-hydroxy-malonic acid diamide, 2,3,4-, 2,3,6- and 3,4,5-trichlorophenyl-hydroxy-malonic acid diamide, 2,3,4,5- and 2,3,5,6-tetrachlorophenyl-hydroxy-malonic acid diamide and pentachlorophenyl-hydroxy-malonic acid diamide.

Formaldehyde-donating compounds which may be mentioned are polymeric formaldehyde, such as metaldehyde or paraldehyde, and formaldehyde acetals, such as formaldehyde diethyl acetal.

Suitable diluents are all inert organic solvents. These include, in particular, aliphatic and aromatic, optionally halogenated hydocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl and dibutyl ether, glycol dimethyl ether and diglycol dimethyl ether, tetrahydrofuran and dioxane, and in addition esters, such as methyl acetate and ethyl acetate, or nitriles, such as, for example acetonitrile and propionitrile, benzonitrile and glutarodinitrile, and furthermore amides, such as, for example, dimethylformamide, dimethylacetamide and N-methylpyrrolidone, as well as dimethyl sulphoxide, tetramethylene sulphone and hexamethylphosphoric acid triamide.

All customary acid-binding agents can be used as bases. These preferably include alkali metal carbonates, hydroxides or alcoholates, such as sodium carbonate or potassium carbonate, sodium hydroxide and potassium hydroxide, sodium methylate, potassium methylate, sodium ethylate and potassium ethylate, and further aliphatic, aromatic or heterocyclic amines, for example trimethylamine, triethylamine, tributylamine, dimethylaniline, dimethylbenzylamine and pyridine.

Suitable acids are Lewis acids, such as boron trifluoride, aluminum trichloride and titanium tetrachloride, and mineral acids, such as sulphuric acid, hydrogen halides and phosphoric acid.

The reaction temperature is kept between about 0°C. and 130°C., preferably between about 20°C. carried out under atmospheric and 60°C. The process is preferably carried out under atmospheric pressure.

When the reaction is complete, the reaction mixture can be worked up in a customary manner in order to isolate the compounds of the formula I, in which $R^9$ represents OH. However, the reaction mixture can also be used directly for further reaction with amines.

For this purpose, as the reaction mixture, in one of the stated solvents, preferably in ethers, such as dioxane or dialkyl ethers, or in ketones, such as acetones, occupied by at least an equimolar amount of the amine components, acidic and basic catalysts being employed in the customary manner. The reaction is carried out to completion at between 0°C. and 130°C., preferably 40°C.-80°C., 1 to 6 hours usually being required for this.

Catalysts which may be mentioned are the acidic and basic catalysts mentioned for carrying out the reaction with formaldehyde. The acidic catalysts are preferred.

The following may be mentioned as amines which can be employed: methylamine, ethylamine, propylamine, isopropylamine, butylamine, iso-butylamine, tert.-butylamine, hexylamine, dodecylamine, 2-ethylhexylamine, tetradecylamine, hexadecylamine, octadecylamine, allylamine, 2-methoxyethylamine, 2-ethoxypropylamine, 3-butoxypropylamine, 2-methylpropyl 3-aminopropanoate, 6-aminohexanitrile, lysine esters, 1,1-aminoundecanoates, cyclohexylamine, trimethylcyclohexylamine, 2-borbornylmethylamine, aniline, o,m,p-chloroaniline, 2,3-, 2,4-, 2,5- and 2,6-dichloroaniline, 3,4- and 3,5-dichloroaniline, p-o-nitroaniline, m,o,p-tolylamine, 3-trifluoromethylaniline, 3-chloro-4-methylaniline, 4-chloro-3-methylaniline, benzylamine, phenylcyclohexylamine and naphthylamine, as well as sec.amines, for example dimethylamine, diethylamine, morpholine, piperidine, piperazine, pyrazole and imidazole.

When the reaction is complete, the compounds of the formula I are isolated in a customary manner.

The compounds of the formula I in which the radical $R^8$ has the meaning other than hydroxyl can be prepared by a variant of the process. To do this, the compounds of the formula II are brought to reaction with formaldehyde and the amines in a single-stage synthesis. In this procedure, the reaction is carried out as follows: the components are stirred in at least an equimolar ratio, preferably with 3 to 6 times the amount, relative to the compounds of the formula II, of formaldehyde, and the same excess amount of amine, in one of the stated solvents, particularly preferably dioxane, diethyl ether, tetrahydrofuran or acetone, with the catalyst, for example potassium carbonate or boron trifluoride etherate, at temperatures between 30°C. and 100°C.

The active compounds are well tolerated by plants, have a favorable level of toxicity to warm-blooded animals, and are suitable for combating animal pests, especially insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Balniulus guttulatus.* From the order of the Chilopoda, for example, *Geophilus carpophagus* and Scutigera spec. From the order of the Symphyla, for example, *Scutigerella immaculata.* From the order of the Thysanura, for example *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides,* Melanoplus *differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia Litura,* Spodoptera spp., *Trichoplusia ni, Carpocapsa pomenella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capus reticulana, Cho-ristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata,*

*Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro*,Argas spp., Ornithodoros spp., *Dermanyssus. gallinae, Eriophyes ribis, Phyllocoptruta oleivora*, Boophilis spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketons, such as acetone, methyl ethyl ketone, methyl isoutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers, there are suitable: for example ground natural minerals, such as kaolins, clays, talc, chalk, quartz, attapulgite, montmorillonite or diatomaceous earth, and ground synthetic materials, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meats, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersin agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides.. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites, preferably ectoparasitic insects in the field of animal husbandry and animal breeding.

The active compounds according to the invention are used in a known manner, such as by oral administration and by dermal application, for example in the form of dipping, spraying, pouring-on and spotting-on, and dusting.

PREPARATION EXAMPLES

Preparation of the starting substances

Example a

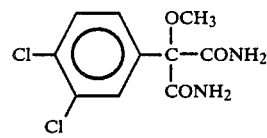

30 g (0.114 mol) of 3,4-dichloro-phenyl-hydroxymalonic acid diamide in 60 ml of dimethyl sulphoxide are initially taken. Thereafter, 6.38 g (0.144 mol) of potassium hydroxide in 150 ml of water are added dropwise, followed by the dropwise addition of 16.1 g (0.114 mol) of methyl iodide. The reaction is exothermic, the temperature increasing to about 50° C. The mixture is allowed to cool, and stirring is continued for 16 hours at 20° C. The precipitated solid is filtered off under suction and washed with water and then with petroleum ether. After recrystallization from ethyl acetate, 14.1 g (44.3% of theory) of 2-(3,4-dichlorophenyl)-2-methoxymalonic acid diamide of melting point 211 to 213° C. are obtained.

Example b

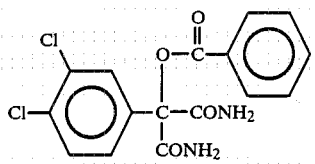

13.1 g of 3,4-dichlorophenylhydroxymalonic acid diamide in 200 ml of benzoyl chloride were heated to 110° C. for 9 hours. Thereafter, the mixture was cooled to 5° C., and the precipitate was filtered off under suction, washed with toluene and then recrystallized from 550 ml of i-propanol. 10 g of 3,3-dichlorophenylbenzoyloxymalonic acid diamide were isolated: m.p. 225° C., with decomposition.

Example c

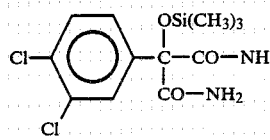

3 g (0.0114 mol) of 3,4-dichloro-phenyl-hydroxymalonic acid diamide, 1.12 g (0.0114 mol) of trimethylsilyl cyanide and 0.9 g (0.0114 mol) of pyridine are heated to 100° C. (bath temperature) for 6 hours. After the pyridine dine has been removed under the vacuum from a water pump, the residue is recrystallized from petroleum ether.

3.45 g (90.3 g of theory) of 2-(3,4-dichlorophenyl)2-trimethylsilyloxy-malonic acid diamide of melting point 156° C. are obtained.

EXAMPLE 1

78 g (0.3 mol) of 3,4-dichlorophenyl-hydroxymalonic acid diamide and 27 g of paraformaldehyde (0.9 mol) in 1 liter of acetone are stirred under reflux with 0.5 g of potassium carbonate for 15 minutes, after which the mixture is filtered while hot. On cooling, N,N'-bishydroxymethylene-3,4-dichlorophenyl-hydroxymalonic acid diamide is precipitated. M.p. 118°-120° C., yield 43 g (49% of theory). The mother liquor predominantly contains the monohydroxymethylene product.

EXAMPLE 2 1:1 mixture of mono- and bishydroxymethylene product:

78 g (0.3 mol) of the starting material as in Example 1 are boiled with 27 g of paraformaldehyde and 0.5g of calcium oxide in 1 liter of acetone for 15 minutes, and the mixture is filtered while hot and then evaporated down. A colorless oil remains which is a 1:1 mixture of the mono- and bishydroxymethylene product of 3,4-dichlorophenyl-hydroxymalonic acid diamide.

EXAMPLE 3

Bis-piperidinomethylene product:

5.2 g (0.02 mol) of 3,4-dichlorophenyl-hydroxymalonic acid diamide and 4 g of 37% strength aqueous formaldehyde maldehyde solution are stirred with 3 g of piperidine and 3 drops of boron trifluoride etherate in 50 ml of dioxane at 50° C. After approx. 7 hours, the reaction is interrupted with 0.5 ml of triethylamine, and the reaction mixture is evaporated down. The solid residue is taken up with ether, the mixture is stirred, and the product is filtered off under suction and rinsed with ether. Yield: 6.0 g of bis-piperidinomethylene-3,4-dichlorophenyl-hydroxymalonic acid diamide (66% of theory). Further product can be isolated from the mother liquor. M.p.: 159°-160° C.

EXAMPLE 4

2.5 g of bisdimethylaminomethylene-3,4-dichlorophenyl-hydroxymalonic acid diamide (33% of theory) are obtained analogously to Example 3, using the same amount of mixture, with 5.8 g of 50% strength aqueous dimethylamine solution. M.p.: 98°-100° C. When gaseous dimethylamine is used, 5.8 g of product are obtained (77% of theory).

EXAMPLE 5

3.21 g of bishydroxymethylene-3,4-dichlorophenyl-hydroxymalonic acid diamide (0.01 mol) are kept at 50° C. with 3 g of piperidine and 3 drops of boron trifluoride in 50 ml of dioxane for 8 hours. After the addition of 0.5 ml of triethylamine, the mixture is evaporated down, the residue is taken up with ether, and the product is filtered off under suction. 6.7 g of bis-piperidinomethylene-3,4-dichlorophenyl-hydroxymalonic acid diamide (73% of theory) of melting point 195° C. are obtained.

EXAMPLE 6

5.2 g of the starting compound from Example 1 are stirred with 3.2 g of 37% strength aqueous formalin solution and 2 g of morpholine in 20 ml of dioxane and 2 ml of concentrated sulphuric acid for 6 hours at 40° C. After 4 ml of triethylamine have been added, the mixture is evaporated down in vacuo, and the residue is taken up with 30 ml of diethyl ether. The precipitated solid is a 1 mixture of mono- and bis-morpholinomethylene-3,4-dichlorophenyl-hydroxymalonic acid diamide. Yield: 3.7 g.

Example A

Critical concentration test/root-systemic action
Test insect: Phaedon cochleariae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/1), being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the following compounds from the preparation examples have a superior action compared to the prior art: 1 and 6

TABLE A

Root-systemic action
Phaedon cochleariae Larvae

| Active compound (constitution) | Degree of destruction in % at an active compound concentration in ppm |
|---|---|
| [Structure: dichlorophenyl-C(OH)(CONH$_2$)-CONH$_2$] known | 2.5 ppm = 0% |
| [Structure: dichlorophenyl-C(OH)(CONH$_2$)-CONH$_2$ + 2 CH$_2$O] according to the invention | 2.5 ppm = 95% |
| [Structure: dichlorophenyl-C(OH)(CONH$_2$)-CONH$_2$ + 1 CH$_2$O] | 2.5 ppm = 100% |

Example B

Critical concentration test/soil insects
Test insect: Phorbia antiqua grubs in the soil
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

Active compounds, amounts applied and results can be seen in Table B:

TABLE B

Soil insecticides
Phorbia antiqua maggots in the soil

| Active compound (constitution) | Degree of destruction at % in active compound concentration in ppm |
|---|---|
| [Structure: dichlorophenyl-C(OH)(CONH$_2$)-CONH$_2$] known | 20 ppm = 0% |
| [Structure: dichlorophenyl-C(OH)(CONH$_2$)-CONH$_2$ + 2 CH$_2$O] according to the invention | 20 ppm = 95% |

It will be understood that the specification and examples are illustrative but not limitative of the present invention and that other embodiments within the spirit and scope of the invention will suggest themselves to those skilled in the art.

We claim:

1. A Substituted malonic acid diamide of the formula $$R^1-C\begin{array}{c}O-R^2\\|\\\phantom{R^1-}CO-N-R^3\\|\\\phantom{R^1-}CO-N-R^4\\|\\\phantom{R^1-}R^8\end{array}\quad R^7$$

wherein
R$^1$ represents aryl or heteroaryl, each of which can optionally be substituted,
R$^2$ represents hydrogen or trialkylsilyl, and represents alkyl, cycloalkyl, alkenyl, alkinyl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl or arylalkylaminosulphonyl, each of which can optionally be substituted, and represents radicals of the formula

—CO—NR$^5$R$^6$ wherein
R$^5$ and R$^6$ independently of one another represent hydrogen, alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, it being possible for these radicals to be optionally substituted,
R$^3$ represents hydrogen or the radical R$^4$,
R$^7$ and R$^8$ independently of one another represent hydrogen, alkyl or aryl, and
R$^4$ represents a radical of the formula

—CH$_2$—R$^9$ and
R$^9$ represents hydroxyl, alkoxy or aryloxy, each of which can optionally be substituted, alkylamino, arylamino, aralkylamino, dialkylamino, diarylamino, cycloalkylamino, alkenylamino, or nitrogen-containing saturated heterocyclic radicals which are bonded via N and optionally contain further hetero atoms.

2. A compound according to claim 1, wherein such compound is N,N'-bis-hydrozymethylene-3,4-dichlorophenylhydroxymalonic acid diamide of the formula

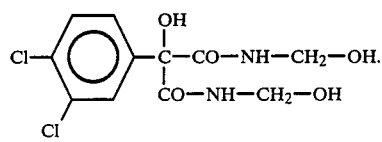

3. A compound according to claim 1, wherein such compound is bis-piperidinomethylene-3,4-dichlorophenylhydroxymalonic acid diamide of the formula

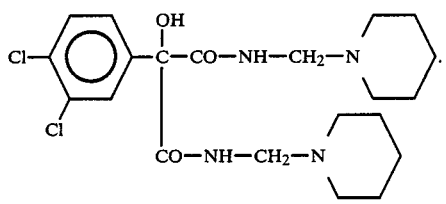

4. A compound according to claim 1, wherein such compound is morpholinomethylene-3,4-dichlorophenylhydroxymalonic acid diamide of the formula

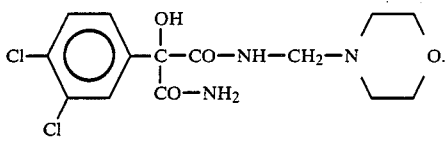

5. A compound according to claim 1, wherein such compound is bis-morpholinomethylene-3,4-dichlorophenylhydroxymalonic acid diamide of the formula

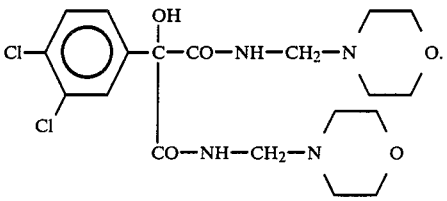

6. An insecticidal composition comprising and insecticidally effective amount of a compound according to claim 1 in admixture with a diluent.

7. A method of combating insects which comprises applying to the insects or to an insect habitat an insecticidally effective amount of a compound according to claim 1.

8. The method according to claim 7, wherein such compound is
N,N'-bis-hydroxymethylene-3,4-dichlorophenylhydroxymalonic acid diamide,
bis-piperidinomethylene-3,4-dichlorophenylhydroxymalonic acid diamide,
morpholinomethylene-3,4-dichlorophenylhydroxymalonic acid diamide or
bis-morpholinomethylene-3,4-dichlorophenylhydroxymalonic acid diamide.

* * * * *